United States Patent
Andersson et al.

(10) Patent No.: US 6,506,187 B1
(45) Date of Patent: Jan. 14, 2003

(54) ABSORBENT ARTICLES THAT INCLUDE LIQUID BARRIERS

(75) Inventors: Mikael Andersson, Göteborg (SE); Ingegerd Carlberg, Vallda (SE); Anita Nyberg, Göteborg (SE); Elisabeth Engström, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/489,611

(22) Filed: Jan. 21, 2000

(30) Foreign Application Priority Data

Jan. 22, 1999 (SE) .............................................. 9900187

(51) Int. Cl.⁷ .................................................. A61F 13/15
(52) U.S. Cl. ........................... 604/385.28; 604/385.01; 604/385.24; 604/385.25
(58) Field of Search .................. 604/381–383, 604/385.08, 385.24–385.28

(56) References Cited

U.S. PATENT DOCUMENTS

| | | | |
|---|---|---|---|
| 4,738,677 A | | 4/1988 | Foreman ...................... 604/385 |
| 4,816,025 A | | 3/1989 | Foreman ................... 604/385.2 |
| 4,887,602 A | * | 12/1989 | O'Leary ................. 604/385.25 |
| 4,900,317 A | * | 2/1990 | Buell ............................ 604/370 |
| 4,938,755 A | | 7/1990 | Foreman ................... 604/385.2 |
| 5,087,255 A | | 2/1992 | Sims ......................... 604/385.1 |
| 5,180,620 A | | 1/1993 | Mende ......................... 428/138 |
| 5,188,627 A | * | 2/1993 | Igaue et al. .................. 604/358 |
| 5,672,166 A | * | 9/1997 | Vandemoortele ........... 604/385.2 |
| 5,718,698 A | * | 2/1998 | Dobrin et al. ............... 604/383 |
| 5,931,825 A | * | 8/1999 | Kuen et al. .............. 604/385.2 |
| 5,947,949 A | * | 9/1999 | Inoue et al. .............. 604/385.2 |
| 6,045,545 A | * | 4/2000 | Vandemoortele et al. 604/385.2 |

FOREIGN PATENT DOCUMENTS

| | | |
|---|---|---|
| EP | 0 409 535 | 1/1991 |
| EP | 0 745 367 | 12/1996 |
| GB | 2 188 532 | 10/1987 |
| WO | 92/07533 | 5/1992 |

* cited by examiner

Primary Examiner—Aaron J. Lewis
Assistant Examiner—C. L Anderson
(74) Attorney, Agent, or Firm—Burns, Doane, Swecker & Mathis, L.L.P.

(57) ABSTRACT

There is provided an absorbent article, such as a diaper, a pant diaper or an incontinence protector that includes longitudinally extending edges and transversally extending edges, a bottom liquid-impermeable sheet, an absorbent layer, longitudinally extending liquid barriers fastened along or on the longitudinal edges of the article, side-flaps which extend laterally outside the liquid barriers and a first upper, essentially liquid-permeable surface sheet between said liquid barriers and a second upper, essentially liquid-impermeable surface sheet outwardly of said liquid barriers, wherein the ends of the liquid barriers are folded down at the front and/or rear end-part and fastened flat against the first and/or the second upper surface sheet. Those areas of the surface sheets situated at the front and/or the rear end-part are comprised of essentially liquid-impermeable material or are covered with essentially liquid-impermeable material. At least a part of said areas has been made permeable to liquid, preferably by perforating said part, down to the absorbent layer which extends beneath at least portions of said part. That part which has been made permeable to liquid is located within at least parts of the downwardly folded ends of the liquid barriers and/or the second surface sheet.

18 Claims, 4 Drawing Sheets

FIG.9

ABSORBENT ARTICLES THAT INCLUDE LIQUID BARRIERS

BACKGROUND OF THE INVENTION

An absorbent article includes, among other things, a bottom liquid-impermeable backing sheet, an absorbent sheet or layer on top of the backing sheet, and an uppermost liquid-permeable surface sheet which is intended to lie proximal to the wearer in use. The sheets are delimited by two transverse edges and two longitudinal edges. When the absorbent article is a diaper or an incontinence protector, the transverse edges will form waist edges and the longitudinal edges will form leg edges. The diaper will then include a front and a rear end-part and an intermediate crotch part which, in use, will lie between the wearer's thighs. So that the article will fit the wearer, it is provided with side-flaps that extend laterally beyond both sides of the absorbent body and at least within that part, which is intended to form the crotch part when using, longitudinal elastic devices along the free side-edges of the side-flaps. The elastic devices serve as leg elastic when the article is worn and are intended to abut the wearer's thighs and shape the article. The flexible side-flaps form sealing edges and are intended to prevent liquid and faeces from leaking out at the edges, in other words they form barriers.

In order to further escape the risk of leakage at the side edges, some absorbent articles also include additional, inner liquid barriers or cuffs, also called standing barriers, fastened in the proximity of the longitudinal edges of the article. The liquid barriers are intended to prevent liquid leaking out at the edges of the absorbent article and also to prevent leakage of any solid matter, such as faeces. This further liquid barrier is positioned inwardly of the leg elastic, i.e. the outer liquid barrier, and is normally made of an essentially liquid-impermeable material, e.g. nonwoven material, although it may alternatively be made of a liquid-permeable material. The liquid barrier is comprised of a web of material whose one longitudinal edge is fastened to the absorbent article and the other edge, its free edge, is intended to lie against the wearer in use. The free edge is gathered or puckered elastically with the aid of an elastic thread that is enfolded in the edge of the web. Examples of diapers that include liquid barriers are described in WO-A1-9207533, SE-T3-0 264 238 and GB-A-2 188 532, for instance. When the absorbent article has liquid barriers positioned inwardly of the flexible side-flaps, the surface material or top sheet material that is located between the two inner liquid barriers, i.e. located in the liquid acquisition region, will be permeable to liquid, while the surface material or top sheet material outside said liquid barriers will be essentially impermeable to liquid.

In the case, e.g., of diapers that include inner liquid barriers or cuffs, the barriers are positioned so as to lie against the wearer's thighs and buttocks and therewith prevent leakage. A given volume of urine is discharged into the diaper each time the wearer urinates. Since it takes a little time for the urine to penetrate through the surface sheet and be absorbed in the absorbent sheet, or layer, some of the urine will "float" on the surface sheet of the article. It is this volume of urine that the barrier shall prevent from leaking out at the edges of the absorbent article.

One edge of the liquid barrier is fastened to the absorbent article. One way of fastening the barrier is to weld said edge firmly to the surface sheet. The ends of the barrier placed at the transverse edges of the article are often folded down flat against the surface sheet and either welded or glued thereto. Any liquid that comes onto this surface, which is substantially liquid-impermeable, will not be absorbed by the article, but will run out at the edges thereof. This can be the case, for instance, when boys lie on their backs with their penises pointing obliquely to one side/or upwards towards the waist part of the diaper. When they urinate, the urine will land at the front part of the diaper in the vicinity of its transverse edge or longitudinal edge, and possibly on the downwardly folded part of the liquid barrier. The diaper will then leak, normally in the region of the wearer's groins or waist. This can also occur in respect of boys that are not lying on their backs, but with whom the penis has been "wrongly positioned" when putting on the diaper, such as to point upwards. It has also been found that liquid will leak likewise in the barrier itself. Liquid leaks out at the elastically gathered edge that lies in abutment with the wearer. Because the barrier edge that lies in abutment with the wearer is gathered, or puckered, it will include narrow through-passing pores or channels in the contact surface between the barrier and the wearer's skin. Liquid is able to penetrate through these pores or channels, when the liquid pressure is excessively high. Folds and pleats can also form in the barrier edge, therewith resulting in liquid escaping at said edge. Surface material that is substantially impermeable to liquid is normally present outwardly of the barrier and any liquid that leaks out will "float" on this essentially liquid-impermeable material. In this regard, there is a serious risk of liquid leaking out through the leg elastic, the outer barrier.

The object of the invention is to solve these problems.

SUMMARY OF THE INVENTION

The present invention relates to an absorbent article that will reduce leakage primarily at the front end-part of the diaper. According to invention, this is achieved by rendering permeable to liquid at least one part of the essentially liquid impermeable regions of and/or on the surface sheet at a front and/or rear end thereof, so that liquid will be able to penetrate quickly into the underlying absorbent sheet or layer.

The use of perforated material is known in the art, for instance from EP 409 535. This material is used, e.g., as the so-called surface sheet or top sheet in absorbent products. According to this EP-specification, the function of the surface sheet material is to form a bulky nonwoven layer that is soft and allows water and gas to pass readily therethrough and effectively absorb moisture. The perforations are formed in a special way such as to obtain a cylindrical shape, where the vertical extension (the height) of said perforations is at least two times the thickness of the surface sheet material. The diameter of the holes or perforations is also said to have different dimensions. In distinction to this document, the present invention relates to the perforation of the material at the ends of the liquid barriers and in the forward and rearward ends of the side-flaps in said surface sheet. In conventional absorbent articles, these materials are usually essentially liquid-impermeable, but are made permeable to liquid in the present invention so that liquid will pass easily and quickly therethrough. This is preferably achieved by perforating the materials, although the invention also relates to other methods.

There is described in EP 745 367 a diaper that includes plastic film liquid barriers. These barriers shall be liquid impermeable and able to breathe at the same time. This is achieved with a barrier that consists of two mutually spaced sheets of plastic film. A plurality of tubular passageways extend from the outer surface of the barrier to its interior. The passageways are configured so that whereas liquid can readily enter into the passageways it is unable to exit therefrom. They are also preferably placed on respective sheets so as not to be linear with one another. Thus, this barrier will not be permeable to liquid even though liquid can enter the actual barrier. The "breathing" function achieved with the barrier passageways is utilised in the upstanding part of the barrier. According to the present invention, parts of those regions of the surface sheet that are liquid-impermeable or covered with a liquid-permeable material in the forward and/or the rearward end-part thereof are made liquid-permeable so that liquid can be sucked down into the underlying absorbent sheet or layer.

The present invention thus relates to an absorbent article, such as a diaper, an incontinence protector or like article, that includes a front and a rear end-part, an intermediate crotch part which is intended to be placed between the wearer's thighs in use, longitudinal and transversal edges, a bottom liquid-impermeable backing sheet, an absorbent sheet, longitudinally extending liquid barriers fastened along or on the longitudinal edges of the article and including a free, stretchable edge which is gathered or puckered at least at its centre part, side-flaps which extend laterally outside the liquid barriers, and longitudinally extending elastic elements along the free side-edges of said side-flaps at least in said crotch part, said elastic elements functioning as leg elastic when the article is worn, a first essentially liquid-permeable surface sheet or top sheet between said liquid barriers, and a second essentially liquid-impermeable surface sheet or top sheet outwardly of said liquid barriers, wherewith the ends of the liquid barriers are folded down flat at the front and/or the rear end-part and fastened against the first and/or the second surface sheet, and wherewith the regions of the surface sheets in the front and/or rear end-part consist of an essentially liquid-impermeable material or are covered by an essentially liquid-impermeable material, wherewith at least a part of said regions has been made permeable to liquid, preferably by perforating down to the absorbent sheet or layer that extends beneath at least portions of said part; and in that the part of said regions that has been made permeable to liquid is located within at least parts of the downwardly folded ends of the liquid barriers and/or the second surface sheet.

BRIEF DESCRIPTION OF THE DRAWINGS

The invention will now be described in more detail with reference to the accompanying drawings, in which.

DESCRIPTION OF EMBODIMENTS

Figures 1, 2:
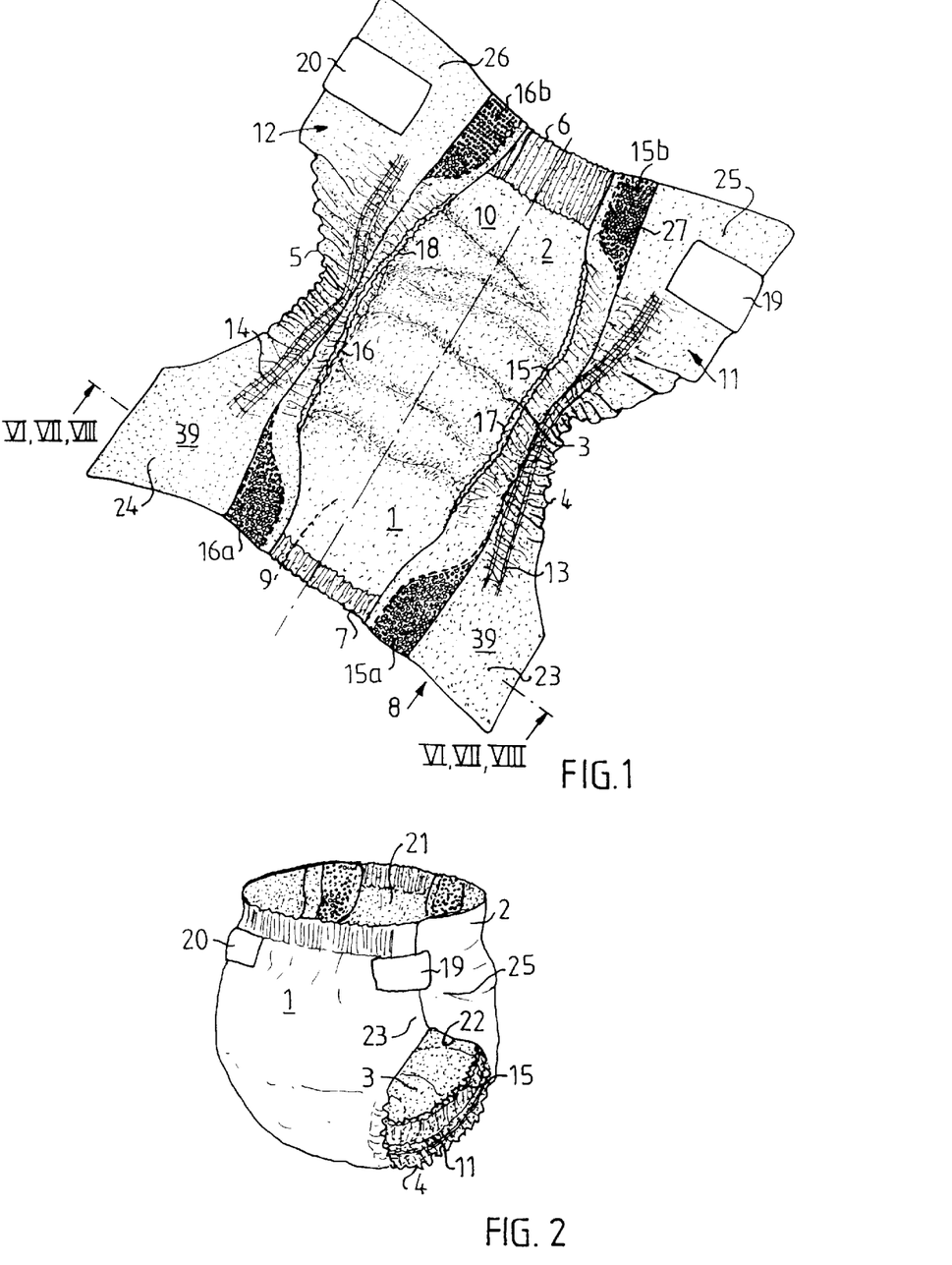
FIG. 1 shows a diaper with the front and rear ends of liquid barriers folded down flat against the front and rear end-parts of the surface sheet.
FIG. 2 shows a diaper configured for use.
Figure 3:
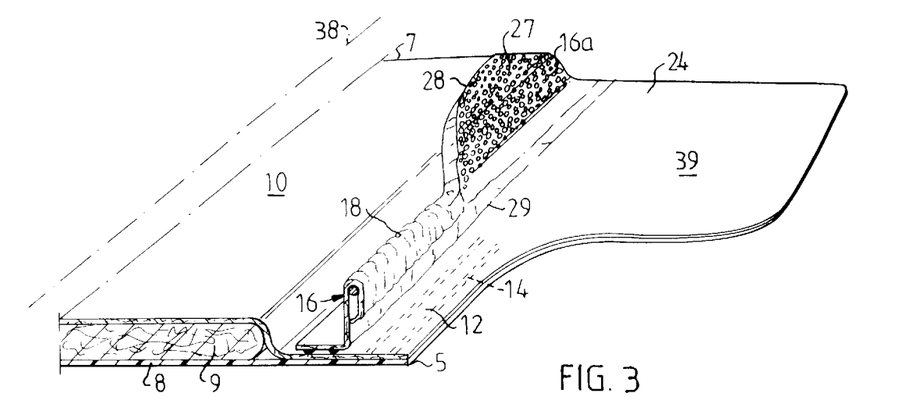
FIG. 3 shows in side view a portion of the front end-part of a diaper comprising the flat, down-folded end of the liquid barrier and the side-flap.

The invention relates to an absorbent article, such as a diaper, an incontinence protector or like article. The following description is made primarily with reference to a diaper. FIG. 1 illustrates a diaper that includes a front and a rear end-part 1, 2, an intermediate crotch-part 3 which is intended to lie between the wearer's thighs in use, longitudinal edges 4, 5 and transversal edges 6, 7, a bottom liquid-impermeable backing sheet 8, an absorbent sheet or layer 9, longitudinally extending liquid barriers 15, 16 fastened along or on the longitudinal edges 4, 5 of said article at a line 29 (see FIG. 3), said barriers including a free, stretchable edge 17, 18 which is gathered or puckered at least at its centre part, side-flaps 11, 12 that extend laterally outside the liquid barriers 15, 16 and that include longitudinally elastic elements 13, 14 along their free side-edges at least in the crotch region 3, said elastic elements 13, 14 functioning as leg elastic when the article is in use, a first upper, essentially liquid-permeable surface sheet or top sheet 10 between the liquid barriers 15, 16 and a second upper, essentially liquid-impermeable surface sheet or top sheet 39 outwardly of said liquid barriers 15, 16, wherewith the ends 15*a*, 16*a*; 15*b*, 16*b* of the liquid barriers are folded down flat at the front end-part 1 and/or the rear end-part 2 and fastened to the first and/or the second surface sheet 10, 39 along a line 28 (see FIG. 3), e.g. glued or welded thereto. The upper surface sheets 10, 39 are intended to lie proximal to the wearer in use. The surface sheets 10 and 39 may consist of one and the same sheet that has different degrees of permeability in the regions corresponding to 10 and 39. Those areas of the surface sheets 10, 39 at the front and/or the rear end-parts 1, 2 thereof consist of generally liquid-impermeable material and/or are covered with liquid-impervious material. In the former case, it may be the material in the second upper surface sheet 39 that is impermeable to liquid, while in the latter case the material in the ends 15*a*, 15*b*; 16*a*, 16*b* of the liquid barriers 15, 16 that are folded down onto one or both of the upper surface sheets that cover the upper surface sheet 10 and thereby create impermeability to liquid. According to the invention, at least one part of these regions has been rendered permeable to liquid, preferably by perforating down to the absorbent sheet or layer 9 that extends beneath at least portions of said part, and said part that has been rendered permeable to liquid is positioned within at least portions of the downwardly folded ends 15*a*, 15*b*; 16*a*, 16*b* of the liquid barriers 15,16 and/or the second surface sheet 39. In the illustrated case, only the down-folded area 15*a*, 15*b*; 16*a*, 16*b* has been perforated, i.e. the whole of this area. It will be understood, however, that it is not necessary to perforate the whole of this area and that solely portions of this area can be perforated in accordance with the invention. The diaper also includes fastener devices 19, 20 (shown folded in against the diaper surface sheet) in the form of adhesive tape or touch-and-close fastener devices. The diaper includes side-flaps 11, 12 which extend slightly beyond the liquid barriers 15, 16. FIG. 3 shows the barrier 16 fastened along a line 29. The side-flaps 11, 12 are considered to lie outside the barrier 15 and 16 and said line 29. The front ends 23, 24 and the rear ends 25, 26 of respective side-flaps 11, 12 can be seen at the front end-part 1 and the rear-end part 2 of the diaper. The longitudinal centre line of the article is referenced 38. Waist elastic of the illustrated diaper may be provided at one or at both of the transverse edges 6, 7, although it is also possible to totally omit waist elastic. Several different types of absorbent article are intended, although primarily diapers, pant diapers and incontinence protectors.

In the FIG. 1 embodiment, the ends 15a, 15b; 16a, 16b of the liquid barriers are folded down inwardly towards the longitudinal centre line 38 of the article. The barriers may be fastened solely at the line 28 and the line 29, where said barriers are fastened at their bottom edge or, alternatively, over the whole of the regions 15a, 16a; 15b, 16b. The barriers may be glued or welded, for instance. The ends that are folded down flat against the upper surface sheet 10, 39 are perforated at at least one end-part. According to the invention, the material may be made permeable to liquid by methods other than perforating methods. Perforation is referred to as a preferred method in the remainder of the description.

FIG. 2 shows the configuration of the diaper when worn. Also shown is the front end-part 1 of the diaper, its rear end-part 2, and the intermediate crotch part 3. The front diaper part 1 is fastened to the rear diaper part 2 with fastener devices 19, 20, while forming at the top of the diaper a waist opening 21 and a respective opening 22 for each of the wearer's thighs. There will be seen at the edge of said opening 22, which is delimited by a longitudinal edge 4 of the article, a side-flap 11 and an upstanding liquid barrier 15. The front end 23 and the rear end 25 of said side-flap 11 are joined together by means of the fastener device 19.

The liquid barriers 15, 16 are gathered or puckered at at least its centre-most part, with the aid of elastic threads that are attached in a stretched state to the free edge of the liquid barrier and fastened at the ends 15a, 15b; 16a, 16b to the surface sheet, or top sheet, 10, 39. Thus, when the article is stretched around the wearer, the liquid barrier will lift to form a standing barrier against the wearer's body. The elastic is stretched during use, causing the barrier to be directed up towards the wearer. As before mentioned, a problem may arise when boys urinate and their penises are directed obliquely forwards, particularly when they are lying on their backs. The urine may then discharge onto the downwardly folded end of the liquid barrier and run out at the front diaper part 1, thus at the forward part of the leg opening 22 or at the region at which the front ends 23, 24 and the rear ends 25, 26 of the side-flaps overlap one another.

The liquid barriers 15, 16 are, at times, essentially liquid impermeable so as to prevent liquid from leaking, primarily in the crotch region 3. Because the liquid barriers 15, 16 are folded down flat against the article at their ends 15a, 15b; 16a, 16b and either glued or welded to the surface sheet 10, 39 at said edge 28, the size of the liquid acquisition part will be reduced, at least when the barriers are folded in towards the centre 38 of the diaper. If liquid should come onto these parts, there is a risk that the liquid will flow out at the edges of the article and soil the wearer's clothes. This problem is solved by the invention, since said parts are perforated so as to enable the liquid to penetrate down to the underlying absorbent sheet or layer 9. Conventional diapers often have an absorbent layer beneath a part of the down-folded end of the liquid barrier. According to the invention, these at least partially perforated areas may have an absorbent layer beneath a part of the perforated sheet or beneath the whole of said sheet. This enhances absorbency in this "leakage risk area".

The liquid barrier 15, 16 is essentially impervious to liquid and shall prevent liquid from leaking primarily in the crotch region of the article. The barrier ends 15a, 16a; 15b, 16b are folded down flat against the surface sheet, and fastened to the diaper. The ends are fastened at the line 28, either by gluing or welding, e.g. ultrasonic welding. These down-folded regions 15a, 16a; 15b, 16b will thus be liquid-impervious, and should liquid come into said areas there is a risk that the liquid will flow out at the edges of the article and onto the wearer's clothes and soil the same. This problem is solved in accordance with the invention, by perforating the down-folded area of the liquid barriers so as to allow said liquid to pass through to the underlying absorbent layer or sheet 9.

FIG. 3 illustrates part of a diaper and shows the end 16a of the liquid barrier folded down flat against the first upper surface sheet 10, inwardly towards the centre line 38. The sectioned view of the diaper shows the bottom liquid-impermeable sheet 8, the absorbent layer 9, the first upper, liquid-permeable surface sheet 10, the second upper, liquid-impermeable surface sheet 39. Also shown is part of a longitudinal edge 5, part of a transversal edge 7, part of a side-flap 12 including longitudinally extending elastic elements 14, part of a liquid barrier 16, a free, stretchable edge 18 of said barrier, the front end 24 of a side-flap and the barrier end 16a that is folded down flat against the upper surface sheet 10 and perforated with holes 27. The Figure also shows a line 28 along which the down-folded barrier end 16a is fastened to the surface sheet 10, either by gluing or welding, e.g. ultrasonic welding. The whole of the area 16a between the lines 28 and 29 may be fastened to the surface sheet in the same way. The absorbent layer must extend beneath at least parts of the perforated area 16a in order for the invention to function. Alternatively, the whole of the area 16a may have absorbent layer extending beneath the area 16a.

Figure 4:
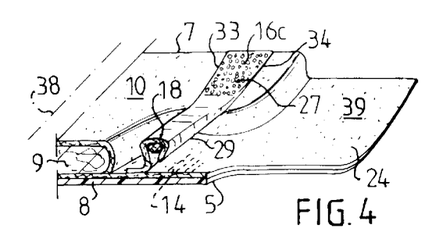
FIG. 4 illustrates a further embodiment of the flat down-folded end of the liquid barrier shown in FIG. 3.

In accordance with another embodiment, down-folding of the front and rear ends 15a, 15b; 16a, 16b of respective liquid barriers may take place outwardly from the diaper centre line 38. The absorbent layer 9 will then extend further out from the longitudinal centre line 38, slightly beyond the liquid barriers 15, 16. FIG. 4 shows an example of an absorbent layer that extends beyond the liquid barrier 16.

According to another embodiment, folding is effected so that the liquid-barrier material will lie flat on both sides of the line 29, where the bottom of the liquid barrier is fastened to the diaper. This embodiment is shown in FIG. 4. The ends 16c of the liquid barriers are folded down flat against the first surface layer 10 inwardly towards the centre line 38 and outwardly from the centre line 38 down against the second surface sheet 39, on respective sides of the liquid-barrier fastener line 29. Perforations 27 are made in the flat, down-folded end 16c so as to allow liquid to pass to the underlying absorbent layer 9 and therewith prevent leakage. The end 16c is fastened along two lines 33, 34 on respective sides of the line 29, against the first surface sheet 10 and the second surface sheet 39 respectively. The whole of the surface of said end 16c may be fastened to the surface sheets 10, 39 also in this case. This method of folding down the ends of the liquid barrier may also be used when said barrier is comprised of a double-folded material and where the two layers are not fastened together but will separate when folded out in two directions. The ends of the liquid barriers may be folded in ways different to those described above in the manufacture of said absorbent articles.

A nonwoven material is normally used as surface sheet material in absorbent articles such as diapers and incontinence protectors. Nonwoven material comprised of polypropylene fibres is one example of such material. This material is hydrophobic, meaning that it will lack affinity for liquid.

This material is suitable for, e.g., the liquid barriers 15, 16 and the outer layer 39 of the side-flaps 11, 12, of which are preferably impervious to liquid. The surface sheet of a diaper may consist of the same material across the whole of said extension, both inwardly and outwardly of the liquid barriers, including the liquid barriers which are then folded from the surface material and which include an elastic thread as an elastic element that provides the gathered part of said barriers. The surface sheet between the two liquid barriers 15, 16 will accept liquid. The side-flaps 11, 12, including their front and rear ends 23, 24, 25, 26 are located outwardly of the liquid barriers 15, 16. As before mentioned, hydrophobic polypropylene nonwoven, which is therewith essentially impermeable to liquid, is a suitable material with respect to the side-flaps and the liquid barriers, since liquid-impermeability is normally desired in this regard. It must be possible for liquid to pass through the liquid acquisition area, or region, between the two liquid barriers 15, 16, so as to reach the absorbent layer 9. The surface sheet is treated in this region so as to be hydrophilic and therewith able to receive liquid and allow said liquid to pass through to the underlying absorbent layer 9. Polypropylene nonwoven can be rendered hydrophilic by conventional methods.

The first and the second surface sheets 10, 39 may consist of one and the same sheet, which extends over the whole of the diaper. In this case, either that part which constitutes the first upper surface sheet 10 between said barriers may be treated so as to be permeable to liquid, or that part which constitutes the second upper surface sheet 39 may be treated so as to be essentially impermeable to liquid. The liquid barriers 15, 16 may also be formed from this sheet, or may consist of a separate sheet of material and be fastened to the upper surface sheets 10, 39. The two surface sheets 10, 39 may alternatively consist of two separate sheets, consisting of one and the same type of material or of different types of material. When the same type of material is used, the surface sheets 10, 39 may have mutually different fibre contents so as to have mutually different densities or thicknesses and therewith allow more or less liquid to pass through. In this case, a denser material is chosen for those areas that shall be impervious to liquid, i.e. the surface sheets 39 of the side-flaps 11, 12 at their front and rear ends 23, 24, 25, 26 and possibly also the liquid barriers 15, 16. A less dense material is used for the liquid acquisition sheet 10 located between the two liquid barriers 15, 16. The materials may initially be hydrophobic and hydrophilic respectively, and the hydrophobic material used at places where the material shall be liquid-impermeable, while the hydrophilic material is used at places where the material shall be permeable to liquid. The liquid barriers 15, 16 may also comprise several and different layers. If the first layer consists of nonwoven, e.g. spun bond nonwoven, which is normal at present, a layer of material can be laid with the aid of melt blowing, this layer being liquid impervious, whereafter a further nonwoven layer can be laid on top of the first-mentioned layer. By melt blowing is meant a technique in which a molten polymer is extruded in a hot gas stream of high velocity and therewith converted into fibres which are cooled and collected to form a fabric or web, which in this case is then bonded to a web of nonwoven fabric. An example of such material is SMS material (spunbond-meltblown-spunbond). This type of layer material may also be used as the surface sheet 39 on the side-flaps 11, 12, which are also essentially impervious to liquid. The liquid barriers 15, 16 are fastened at one edge at the line 29 against the upper surface sheet, or top sheet, of the article and have a free, stretchable edge 17, 18, meaning that the barrier will be lifted up against the wearer and function as a barrier. Other types of liquid-impermeable material may, of course, alternatively be used in these areas of the article. Similarly, different liquid-permeable materials may be used in the liquid-permeable material in the surface sheet 10 between the liquid barriers 15, 16.

Figure 5:
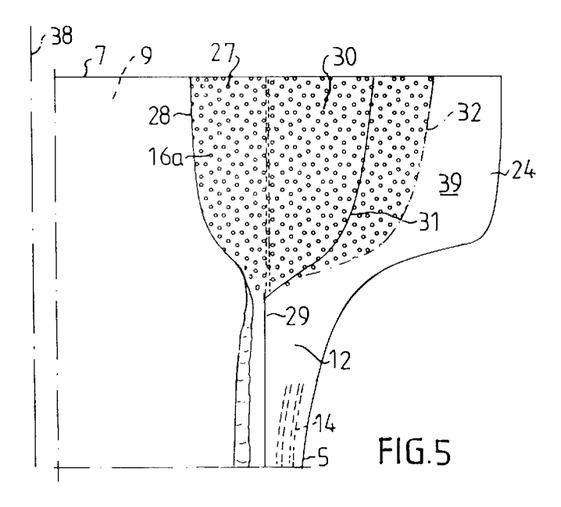
FIG. 5 shows two different embodiments of a portion of the front end-part of a diaper immediately from above.

Two further embodiments of the invention are shown in FIG. 5. The absorbent layer is shown to extend slightly beyond the liquid-barrier fastener line 29, in order to provide a high absorption capacity at the front and rear ends 23, 24, 25, 26 of the side-flaps, where the risk of urine leakage is comparatively high. The absorbent layer may have an I-shape or a T-shape, meaning that the absorbent layer will extend outwards from the longitudinal centre line 38 at its front and/or its rear ends. FIG. 5 illustrates part of a diaper immediately from above. The Figure shows part of a transverse edge 7, part of a longitudinal edge 5, a side-flap 12 that includes elastic elements 14, part of a liquid barrier 16, the front end 24 of a side-flap, and the end 16a of the liquid barrier that is folded down flat against the upper surface sheet 10, towards the centre line 38, and provided with perforations 27. The surface sheet 39 is essentially impervious to liquid at the front and rear ends 23, 24, 25, 26 of the side-flaps, and any liquid deposited thereon will float on this surface and be liable to leak out at the edges of the diaper. This problem is solved by the invention, by perforating the surface sheet 39 at the front and rear ends 23, 24, 24, 26 of the side-flaps, as illustrated in FIG. 5 on one of the front ends 24. This enables liquid to penetrate down to the underlying absorbent layer 9, which extends out in the region of the front and rear ends 23, 24, 25, 26 of the side-flaps. FIG. 5 shows two mutually different embodiments. The perforations extend between the fastening line 29 and the line 32. In one of said embodiments, the absorbent layer 9 extends only to the line 31 and only partially beneath the perforated surface sheet. In the other embodiment, the absorbent layer 9 extends right up to the line 32 and thus beneath the whole of the perforated surface sheet. The perforated part may also extend over the whole of the surface sheet 39 at the front and rear side-flap ends 23, 24, 25, 26. The perforations in these regions or areas are shown in the form of holes 30, as distinct from the holes 27 in the downwardly folded liquid barriers.

Other embodiments are conceivable. For instance, the downwardly folded ends 15a, 15b; 16a, 16b of respective liquid barriers 15, 16 are not always perforated, but solely parts of the second surface sheet 39 in the front and/or rear side-flaps 23, 24, 25, 26. However, it is preferred that these downwardly folded ends 15a, 15b; 16a, 16b are perforated when the liquid barriers 15, 16 consist of an essentially liquid-impermeable material.

Figure 9:
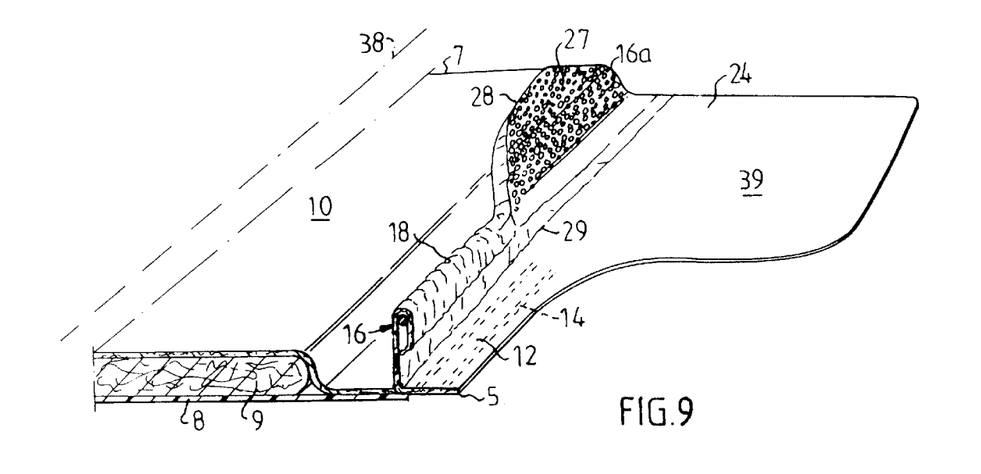
FIG. 9 illustrates an embodiment of the front end-part of a diaper shown in FIG. 3.

FIG. 9 illustrates a further embodiment of the invention, and shows the front end-part of the diaper. In this case, the first upper surface sheet 10 and the second upper surface sheet 39 are two mutually different sheets. The liquid barrier 16 consists of the same material sheet as the second surface sheet 39, by virtue of said sheet being folded up and around an elastic element. In this illustrated embodiment, the liquid-impermeable bottom sheet 8 does not extend right out beneath the side-flap 12. It is not necessary for the bottom sheet to extend to the outer extremity of the side-flap 12, because the second surface sheet 39 is essentially impermeable to liquid. However, when the absorbent layer 9 extends out into the side-flaps, the bottom sheet, or backing sheet, 8 will extend out beneath the side-flaps.

The absorbent material in the front and rear ends 23, 24, 25, 26 of the side-flaps may either be the same as the absorbent material in the remainder of the article or may comprise some other absorbent material. A common material in the absorbent layer 9 is a mat-formed material. Mats are formed by defibring and dry-shaping roll pulp into a web that forms the absorbent layer. Alternatively, there can be used absorbent material taken from a roll that does not need to be defibred prior to being fed to the machine for manufacturing the absorbent article. An example in this latter case is air-laid material with or without an admixture of super-absorbent polymers.

Figure 6:
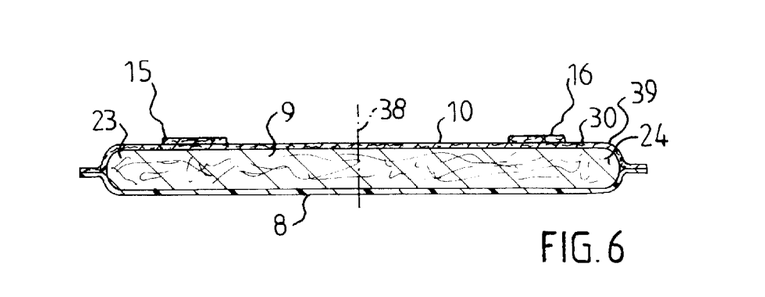
FIG. 6 is a sectional view of the front end-part of a diaper taken on the line VI—VI in FIG. 1.

These absorbent materials can be used in the absorbent layer 9 of the diaper. Mat-formed material can be used in the whole of the absorbent layer 9 and extend out in the regions marked with the lines 31 or 32 in the front and rear ends 23, 24, 25, 26 of the side-flaps. Alternatively, the roll material can be used in the whole of the absorbent layer 9. This is shown in FIG. 6.

Figure 7:
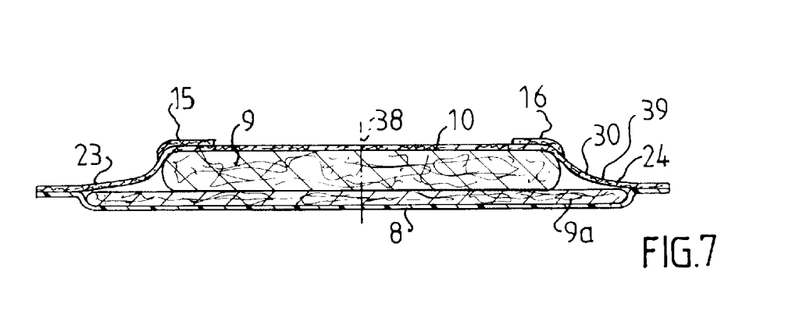
FIG. 7 is a sectional view of the front end-part of a diaper taken on the line VII—VII in FIG. 1.
Figure 8:
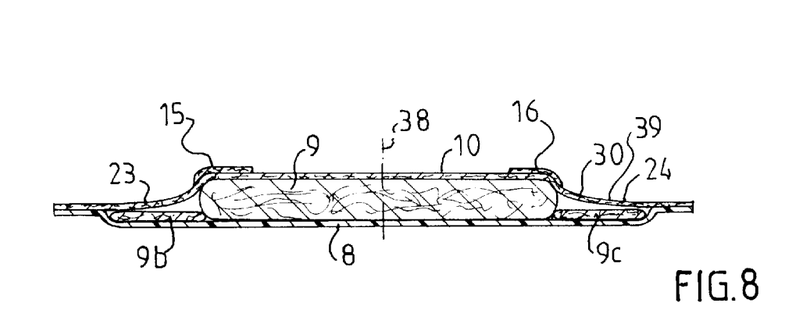
FIG. 8 is a sectional view of the front end-part of a diaper taken on the line VIII—VIII in FIG. 1.

It is also possible to use mat-formed material in the major part of the absorbent layer 9 and roll material in those regions that are situated at the front and rear ends 23, 24, 25, 26 of the side-flaps, these regions being located beneath the perforated areas. FIGS. 7 and 8 illustrate respective examples of the use of mat-formed material and roll material. In the FIG. 7 illustration, a layer 9a of roll material is placed on the liquid-impermeable sheet 8 at least in the front end-part 1 of the diaper. It may also be placed in the rear end-part 2. This layer 9a is topped by the absorbent layer 9, which for example may be a mat-formed material. The layer 9a of roll material extends beneath the whole of the absorbent layer 9, at least at the front and/or rear end-part 1, 2, and extends out at the front and rear ends 23, 24, 25, 26 of the side-flaps beyond the liquid barriers 15, 16 and beneath those regions of the surface sheet at the ends 23, 24, 25, 26 of the side-flaps that are perforated in parts of the surface sheet.

In the FIG. 8 embodiment, roll material is used only in the front and rear ends 23, 24, 25, 26 of the side-flaps, although it is in contact with the absorbent layer 9. The absorbent parts of roll material are referenced 9b and 9c in the Figure. Other absorbent materials may be used and may be arranged in ways other than those described above. They may also contain superabsorbent material, which may be in powder form, fibre form, layered, or in other forms.

The perforated parts located outwardly of the liquid barriers need not be limited to the front and rear side-flap ends 23, 24, 25, 26, but may extend over the whole of the side-flaps 11, 12. This can simplify the manufacture of absorbent articles, since complete surface sheet webs are advanced at high speeds and the whole of the outer edges, the side-flaps, can be perforated. Absorbent layers, however, are not used under the whole of these perforated areas.

The perforations, i.e. the holes 27, 30, have a diameter in the order of from 0.5 mm to 5.0 mm, preferably from 1.0 mm to 4.0 mm. The hole spacing is from 0.5 mm to 5.0 mm, preferably from 1.0 mm to 4.0 mm. The downwardly folded ends 15a, 15b, 15c; 16a, 16b, 16c of the liquid barriers fastened flat against the surface sheet 10, 39 are perforated over an area that extends from one of the transverse edges, or preferably from about 1 cm from said transverse edges, up to about 10 cm, preferably about 6 cm, from the transverse edges 6, 7 along the liquid barrier. These distances also apply to the perforated areas that lie outside the liquid barriers 15, 16 in the front and rear side-flap ends 23, 24, 25, 26.

The hole spacing and the size of said holes will depend on the distance to underlying material, the hydrophilicity of said underlying material and the diameter of the hole, if it is the same liquid that is used. A possible hole diameter is about 2 to 4 mm with a relatively small spacing therebetween, i.e. a spacing of about 2 to 3 mm, so that liquid will not float on the hydrophobic material between said holes. The size of the perforated areas will depend partially on the type of diaper or incontinence protector concerned. Diapers are available in many sizes, from sizes intended for babies that have been born prematurely to adult sizes. The perforated areas will be larger in a large size diaper and smaller in diapers of smaller sizes.

The holes can be made in a conventional manner and the positioning of the perforations has no significance with respect to the type of perforations used. In other words, the holes 27 in the down-folded end of the liquid barrier may be made in the same way as the holes 30 in the front and rear ends of the side-flaps.

The openings formed by the perforations in the material are larger than the interstices or cavities between the fibres in, e.g., nonwoven material or other material which already has narrow openings. Hot needle piercing is an example of one hole forming method, in which hot needles heat the nonwoven material to a temperature slightly beneath its melting point. Another example is one in which material is passed between two rollers and provided with a large number of cuts in the clamping location or nip between raised plateaus on a matrix cylinder and knife edges that extend peripherally around a cutting cylinder. The cuts are mutually spaced from one another. Another perforating method is used in respect of laminates between nonwoven and polyethylene film. A layer of material is passed between a pair of rolls and part of the sheet removed therewith. One of the rolls is a pattern roll that includes several projections or anvils and the second roll is a cutting roll provided with cutting edges. Other examples are punching, or clipping, ultrasound against anvils and laser cutting. Holes can also be formed in material with the aid of water jets that are directed onto the material at very high pressures. Flame perforation is used only for thin plastic film. The choice of method used will depend on the material used and also on the desired appearance of the hole. The holes need not be circular, but may have several different shapes, for instance oval, square or other shapes.

Some types of absorbent article also include liquid barriers along the transverse edges. The invention also includes perforations that are made in flat down-folded parts of these transverse barriers.

Also available are absorbent articles that lack the inner liquid barriers 15, 16 described above. In such cases, the flexible side-flaps 11, 12 with the leg elastic that holds the diaper tight against the thighs of the wearer then constitutes a liquid barrier. The regions of liquid-impermeable material in the front and rear part of such a diaper can be perforated, in order to prevent liquid that "floats" on the surface sheet of said diaper from leaking out at the front and rear side-flaps 23, 24, 25, 26. Liquid will then be sucked down through the holes and into the underlying sheet instead of leaking out at the diaper edges.

The invention thus relates to an absorbent article that has improved properties with respect to leakage at the front and the rear end-part of the article, e.g. a diaper or an incontinence protector. In the regions of the surface sheets 10, 39 in the front and/or rear end-part 1, 2, which consists of an essentially liquid-impermeable material or is covered by an essentially liquid-impermeable material, at least a part of said regions has been made permeable to liquid, preferably by perforating said part so that liquid will be able to pass through to the underlying absorbent layer 9. The liquid-permeable part is located within at least parts of the downwardly folded ends 15a, 15b; 16a, 16b of the liquid barriers 15, 16 and/or the second surface sheet 39. The absorbent layer extends beneath parts of said perforated surface sheet or beneath the whole of the perforated outer sheet.

By "including" as used above is meant including but not limited thereto.

What is claimed is:

1. An absorbent article, comprising:

a front and a rear end-part, an intermediate crotch part intended to be placed between the wearer's thighs in use, longitudinally extending edge regions having longitudinally extending edges, transversely extending edges, a bottom liquid-impermeable sheet, an absorbent sheet or layer, longitudinally extending liquid barriers fastened along or at the longitudinally extending edge regions of said article and including a free stretchable edge which is puckered or gathered at least at its centre part, side-flaps which extend laterally outwardly of the liquid barriers and have longitudinally extending elastic elements along said free stretchable edges at least in the crotch part, said elastic elements serving as leg elastic when the article is worn, a first upper, essentially liquid-permeable surface sheet between said liquid barriers, and a second upper, essentially liquid-impermeable surface sheet outwardly of the liquid barriers, wherein ends of said liquid barriers are folded down at the front or the rear end-part and fastened flat against portions of the first or the second surface sheet, and wherein the portions are permeable to liquid, down to the absorbent layer extending beneath at least the portions; and the downwardly folded ends of the liquid barriers are permeable to liquid and center parts of the liquid barriers between the folded ends are liquid impermeable.

2. An absorbent article according to claim 1, wherein the absorbent layer extends beneath the whole of the part that has been made permeable to liquid.

3. An absorbent article according to claim 1 wherein the ends of the liquid barriers are folded down inwardly towards the longitudinal centre line of the article.

4. An absorbent article according to claim 1, wherein the ends of the liquid barriers are folded down outwardly from the longitudinal centre line of the article.

5. An absorbent article according to claim 1, wherein the ends of the liquid barriers are folded down both inwardly towards the centre line of the article and outwardly from said article centre line on respective sides of the fastener line of said liquid barriers.

6. An absorbent article according to claim 1, wherein the liquid barriers are comprised essentially of liquid-impermeable material; and in that parts of said downwardly folded ends have been made permeable to liquid.

7. An absorbent article according to claim 1, wherein the liquid permeability of said part extends from one of the transversely extending edges along the liquid barrier.

8. An absorbent article according to claim 1, wherein parts of the second surface sheet or the whole of said second surface sheet has been made permeable to liquid at the front or rear ends of the side flaps.

9. An absorbent article according to claim 1, wherein the downwardly folded ends of the liquid barriers or the second surface sheet have been made permeable to liquid with holes having a diameter of from 0.5 mm to 5.0 mm.

10. An absorbent article according to claim 9, wherein the holes are spaced from 0.5 mm to 5.0 mm apart.

11. An absorbent article according to claim 1, wherein said liquid-impermeable parts have been made permeable to liquid solely in the front part of said article.

12. An absorbent article according to claim 1, wherein said absorbent article is a pant diaper.

13. An absorbent article according to claim 1, wherein said absorbent article is an incontinence protector.

14. An absorbent article according to claim 1, wherein the liquid permeability of said part extends from about 6 cm from the transversely extending edges along the liquid barrier.

15. An absorbent article according to claim 1, wherein the downwardly folded ends of the liquid barriers or the second surface sheet have been made permeable to liquid with holes having a diameter of from 1.0 mm to 4.0 mm.

16. An absorbent article according to claim 9, wherein the holes are spaced from 1.0 mm to 4.0 mm apart.

17. An absorbent article according to claim 1, wherein said at least one part of said areas has been made permeable to liquid through the medium of perforations.

18. An absorbent article according to claim 1, wherein the liquid permeability of said part extends from about 1 to 10 cm from the transversely extending edges along the liquid barrier.

* * * * *